US008952895B2

(12) United States Patent
Moore et al.

(10) Patent No.: US 8,952,895 B2
(45) Date of Patent: Feb. 10, 2015

(54) MOTION-BASED DEVICE OPERATIONS

(75) Inventors: Christopher Moore, San Francisco, CA (US); Christopher T. Mullens, San Francisco, CA (US); Gregory Novick, Santa Clara, CA (US); Ronald K. Huang, San Jose, CA (US); William Matthew Vieta, San Jose, CA (US); Xiaoyuan Tu, Sunnyvale, CA (US)

(73) Assignee: Apple Inc., Cupertino, CA (US)

(*) Notice: Subject to any disclaimer, the term of this patent is extended or adjusted under 35 U.S.C. 154(b) by 138 days.

(21) Appl. No.: 13/153,335

(22) Filed: Jun. 3, 2011

(65) Prior Publication Data

US 2012/0306770 A1    Dec. 6, 2012

(51) Int. Cl.
 G06F 3/033   (2013.01)
 G09G 5/08    (2006.01)
 H04M 1/725   (2006.01)
 G06F 3/01    (2006.01)
 G06F 3/0346  (2013.01)

(52) U.S. Cl.
 CPC ............ *H04M 1/72522* (2013.01); *G06F 3/01* (2013.01); *G06F 3/0346* (2013.01); *H04M 2250/12* (2013.01); *H04M 2250/22* (2013.01); *H04M 2250/74* (2013.01)
 USPC ........................................................ 345/158

(58) Field of Classification Search
 CPC .................................................... G06F 3/0346
 USPC ........................................................ 345/158
 See application file for complete search history.

(56) References Cited

U.S. PATENT DOCUMENTS

| 2002/0121972 | A1* | 9/2002 | Schofield et al. ............. 340/438 |
| 2006/0266949 | A1* | 11/2006 | Bender et al. .............. 250/370.1 |
| 2007/0085157 | A1 | 4/2007 | Fadell et al. |
| 2008/0014989 | A1 | 1/2008 | Sandegard et al. |
| 2009/0167719 | A1 | 7/2009 | Wooley |
| 2009/0209293 | A1* | 8/2009 | Louch ........................... 455/566 |
| 2009/0265670 | A1 | 10/2009 | Kim et al. |
| 2010/0321289 | A1 | 12/2010 | Kim et al. |

FOREIGN PATENT DOCUMENTS

EP     2182452      5/2010

OTHER PUBLICATIONS

International Search Report and Written Opinion of the International Searching Authority, PCT Application Serial No. PCT/US2012/036165, Aug. 1, 2012, 11 pages.

* cited by examiner

*Primary Examiner* — Alexander Eisen
*Assistant Examiner* — Mark Regn
(74) *Attorney, Agent, or Firm* — Fish & Richardson P.C.

(57) ABSTRACT

Methods, program products, and systems of motion-based device operations are described. A mobile device can coordinate operations of a motion sensor and a proximity sensor. The mobile device can determine a gesture event using the motion sensor. The mobile device can determine a proximity event using the proximity sensor. The mobile device can use the gesture event and proximity event to confirm one another, and determine that the mobile device has moved in proximity to a target object following a specified gesture. Upon confirmation, the mobile device can perform a specified task.

24 Claims, 11 Drawing Sheets

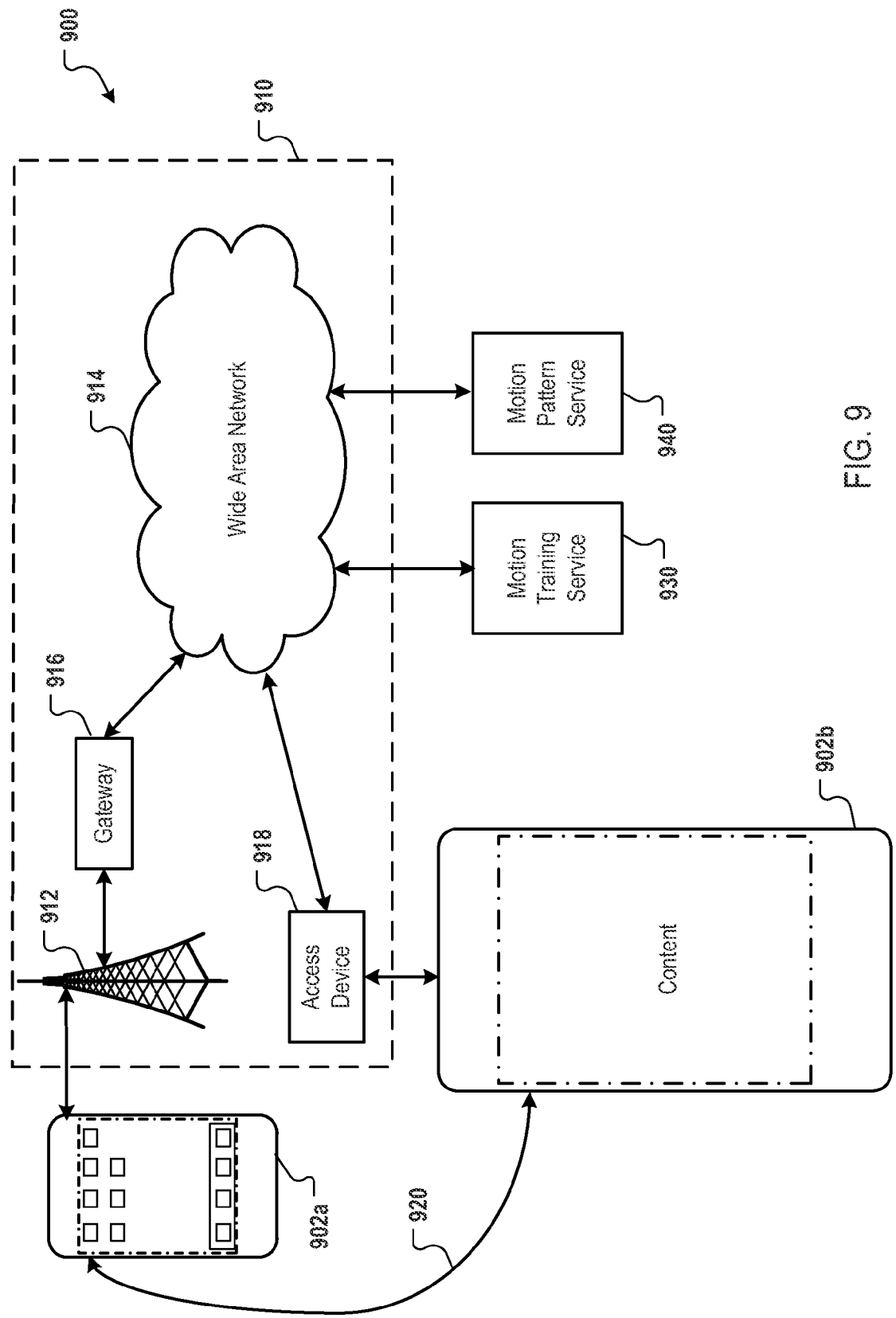

MOTION-BASED DEVICE OPERATIONS

TECHNICAL FIELD

This disclosure relates generally to motion-based operations of a mobile device.

BACKGROUND

A mobile device can include a motion sensor that is configured to detect a motion of the mobile device. The motion sensor can measure movement and rotation of the mobile device in a two-dimensional or three-dimensional space and provide as an output a series of readings of the acceleration. Based on the acceleration readings, the mobile device can determine whether the device is or was in motion. The mobile device can use the motion to control various functions or application programs of the mobile device. For example, the mobile device can use the series of readings as an input to an application program. Based on the motion sensor readings, the application program can perform various tasks.

SUMMARY

Methods, program products, and systems of motion-based device operations are described. A mobile device can coordinate operations of a motion sensor and a proximity sensor. The mobile device can determine a gesture event using the motion sensor. The mobile device can determine a proximity event using the proximity sensor. The mobile device can use the gesture event and proximity event to confirm one another, and determine that the mobile device has moved in proximity to a target object following a specified gesture. Upon confirmation, the mobile device can perform a specified task.

In general, in one aspect, motion-based device operations can include receiving program instructions configured to cause the mobile device to perform a task upon detecting that the mobile device has moved to a location proximate to an object. The operations can include obtaining a motion reading from one or more motion sensors of a mobile device; detecting a gesture event based on the motion reading, including determining that the motion reading indicates that the mobile device moves towards a target object in one or more specified fashion; detecting a proximity event, including obtaining a proximity reading from a proximity sensor of the mobile device, the proximity reading indicating that the mobile device is located proximate to an object; determining, based on the gesture event and the proximity event, that the mobile device has moved to the location proximate to the target object; and then performing a task in response.

Motion-based device operations can be implemented to achieve the following advantages. False positive rates of gesture recognition or proximity determination can be lowered compared to conventional mobile devices. When the mobile device moves in a manner that is similar to a specified gesture, the mobile device can designate the movement as the gesture after confirmation from a proximity sensor. An interrupted movement can be filtered out. Thus, for example, if a user moves a mobile device from a pocket to an ear, the mobile device need not activate a voice input function until the mobile device reaches the ear.

In addition, response time of a mobile device can be shortened, comparing to conventional mobile devices. A proximity sensor of a mobile device may need calibration before proximity detection. The mobile device can calibrate the proximity sensor before the mobile device reaches an object, based on motion sensor readings. Thus, when the mobile device reaches the object, the proximity sensor can be already calibrated. If a task requires a proximity sensor input, the proximity sensor can appear to respond almost instantaneously, from a user's point of view.

The details of one or more implementations of motion-based device operations are set forth in the accompanying drawings and the description below. Other features, aspects, and advantages of motion-based device operations will become apparent from the description, the drawings, and the claims.

BRIEF DESCRIPTION OF THE DRAWINGS

FIG. 9 is a block diagram of exemplary network operating environment for the mobile devices configured to perform motion-based operations.

Like reference symbols in the various drawings indicate like elements.

DETAILED DESCRIPTION

Overview of Motion-Based Device Operations

Figure 1:
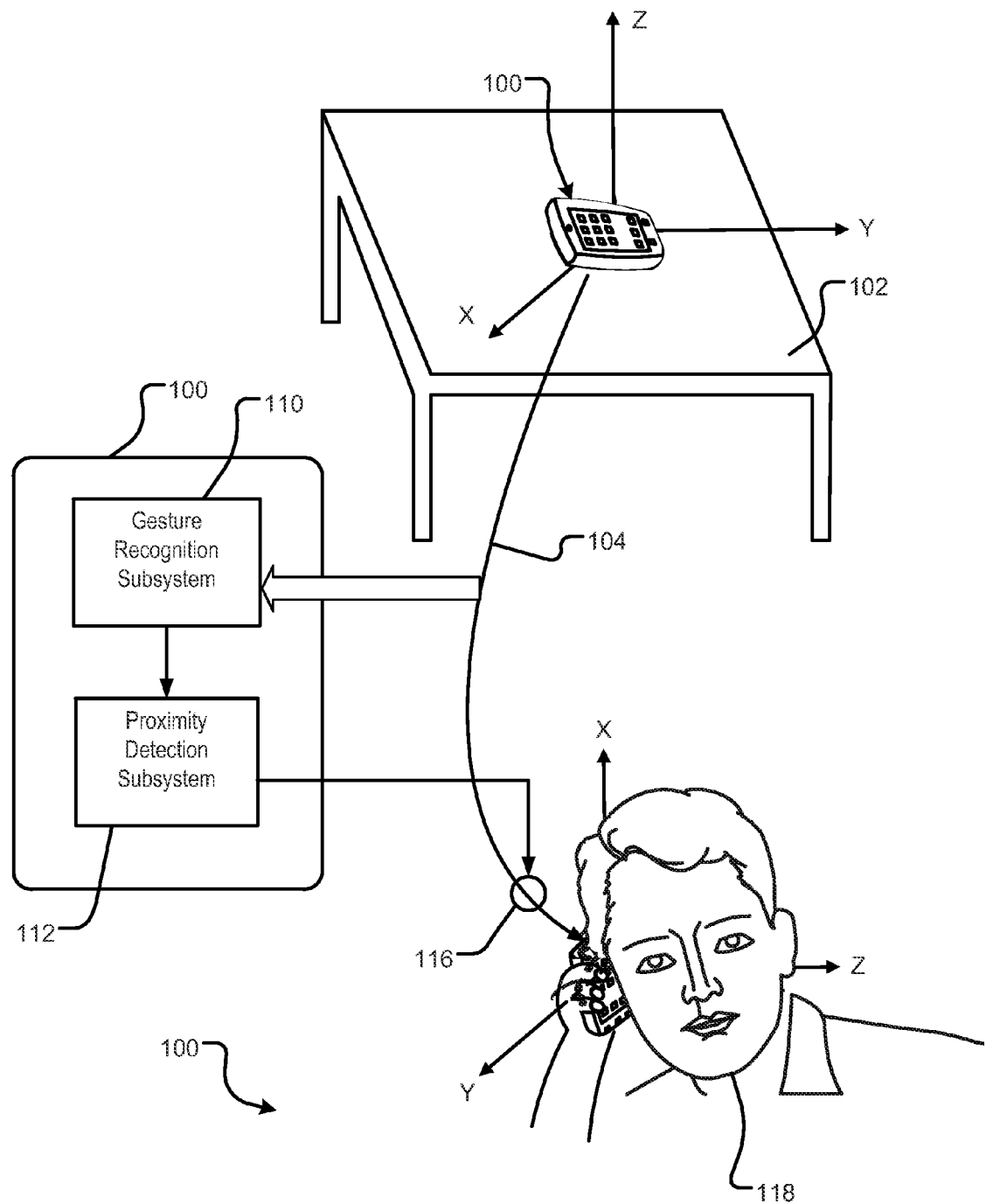
FIG. 1 is a diagram that provides an overview of exemplary motion-based device operations.

FIG. 1 is a diagram that provides an overview of exemplary motion-based device operations. Mobile device 100 is a device configured to perform a task in response to a gesture. The gesture can include a user action of picking up mobile device 100 from an initial position and putting mobile device 100 near face 118.

In the example shown, the initial position of mobile device 100 is a face-up position on table 102. Mobile device 100 is then picked up from a table and moved to a face, following motion path 104. Mobile device 100 can track motion path 104 using a motion sensor. The motion sensor can be configured to measure linear acceleration values, angular rate values, or both, of mobile device 100 on multiple axes (e.g., X, Y, Z or pitch, yaw, roll) and generate motion sensor readings. The motion sensor readings can include a time series of motion vectors corresponding to motion path 104.

Mobile device 100 can include gesture recognition subsystem 110. Gesture recognition subsystem 110 is a component of mobile device 100 that is configured to recognize a gesture from various motions. For example, a gesture of picking up mobile device 100 from an initial position and putting mobile device 100 near face 118 can be performed by a left hand or a right hand, quickly or slowly, with or without an interruption (e.g., an action of turning mobile device 100 for viewing a display before putting it near an ear). Gesture recognition subsystem 110 can recognize the gesture from these variations based on one or more motion patterns. Further details of the operations of gesture recognition subsystem 110 will be described below in reference to FIGS. 3 and 4A-4B.

Mobile device 100 can include proximity detection subsystem 112. Proximity detection subsystem 112 is a component of mobile device 100 that is configured to detect a proximity event. Mobile device 100 can use the proximity event to confirm a recognized gesture and reduce false positives. A false positive is an occurrence that movement of mobile device is mistakenly recognized as a designated gesture. For example, when a mobile device is taken out of the pocket and put on a table, the mobile device can mistakenly determine that a gesture of picking up the mobile device is received. By employing one or more other sensors of mobile device 100, proximity detection subsystem 112 can detect a false positive when a condition of the mobile device is inconsistent with a normal consequence of the gesture. For example, mobile device 100 can identify a false recognition of a gesture of moving mobile device 100 to face 118 when, after the movement, a proximity sensor fails to detect face 118. Mobile device 100 can confirm the gesture when proximity detection subsystem 112 detects a proximity event shortly after or shortly before gesture recognition subsystem 110 recognizes the gesture (e.g., at time 116).

Likewise, mobile device 100 can use a gesture detected by gesture recognition subsystem 110 to confirm a proximity event. For example, mobile device 100 may detect a proximity event when a user places a hand near a proximity sensor of mobile device 100, or places mobile device near an ear. Based on a gesture determined by gesture recognition subsystem 110, mobile device 100 can determine whether the proximity event is caused by the user placing mobile device 100 near the ear. Mobile device 100 can turn off a display screen when a gesture of putting the mobile device near an ear occurred approximately at the same time. Thus, mobile device 100 can avoid turning off the display screen when a user merely places a hand near the display screen.

Upon the confirmation of the gesture, mobile device 100 can perform various tasks. For example, mobile device 100 can deactivate a touch-screen input device, or activate a voice input device, or both. Based on characteristics of the confirmed gesture input, mobile device 100 can set the voice input device to various input modes.

Figure 2:
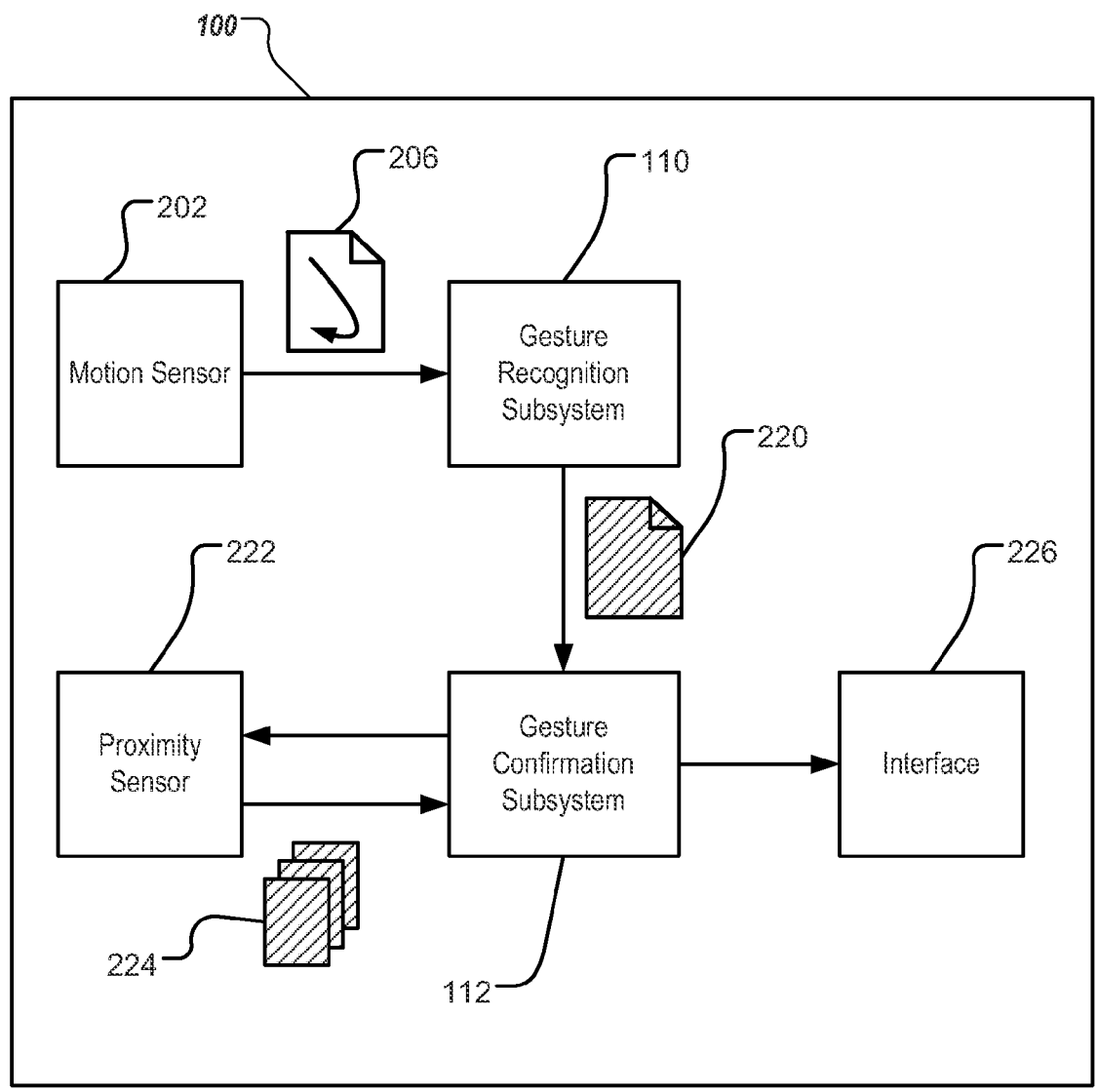
FIG. 2 is a block diagram of an exemplary mobile device configured to perform motion-based operations.

FIG. 2 is a block diagram of an exemplary mobile device 100 configured to perform motion-based operations. Mobile device 100 can include motion sensor 202. Motion sensor 202 can continuously monitor motions (including linear accelerations, or angular rates, or both) of mobile device 100 and generate motion sensor readings 206. Mobile device 100 can include gesture recognition subsystem 110 that is configured to receive the motion sensor readings 206 and generate a recognized gesture 220. The recognized gesture 220 can include an identifier of the gesture (e.g., "picking up" or "putting down"). In some implementations, recognized gesture 220 can be associated with a timestamp. The timestamp can indicate a beginning time of the gesture, an end time of the gesture, or any time in between.

Mobile device 100 can include proximity detection subsystem 112 that is configured to confirm recognized gesture 220. If the recognized gesture 220 is a gesture that usually results in proximity between mobile device 100 and an object, proximity detection subsystem 112 can configure proximity sensor 222 to detect the proximity. Proximity sensor 222 can include a component of mobile device 100 that is configured to detect presence of a nearby object without physical contact between mobile device 100 and the object. When proximity detection subsystem 112 receives recognized gesture 220, proximity detection subsystem 112 can change an operating mode of the proximity sensor from a passive mode to an active mode. In the active mode, the proximity sensor can detect a nearby object (e.g., human face 118) and produce proximity output 224. Proximity output 224 can be a binary value (e.g., "yes" or "no") or a scale value indicating a likelihood that mobile device 100 is near an object, or indicating a distance between the mobile device and an object.

Based on proximity output 224, proximity detection subsystem 112 can determine whether to confirm recognized gesture 220. If proximity detection subsystem 112 confirms recognized gesture 220, proximity detection subsystem 112 can notify interface 226. Interface 226 can include an application programming interface (API) of a system function or an application program. Upon receiving the confirmation through interface 226, the system function or the application program can perform a task based on recognized gesture 220.

Operations of an Exemplary Gesture Recognition Subsystem

Figure 3:
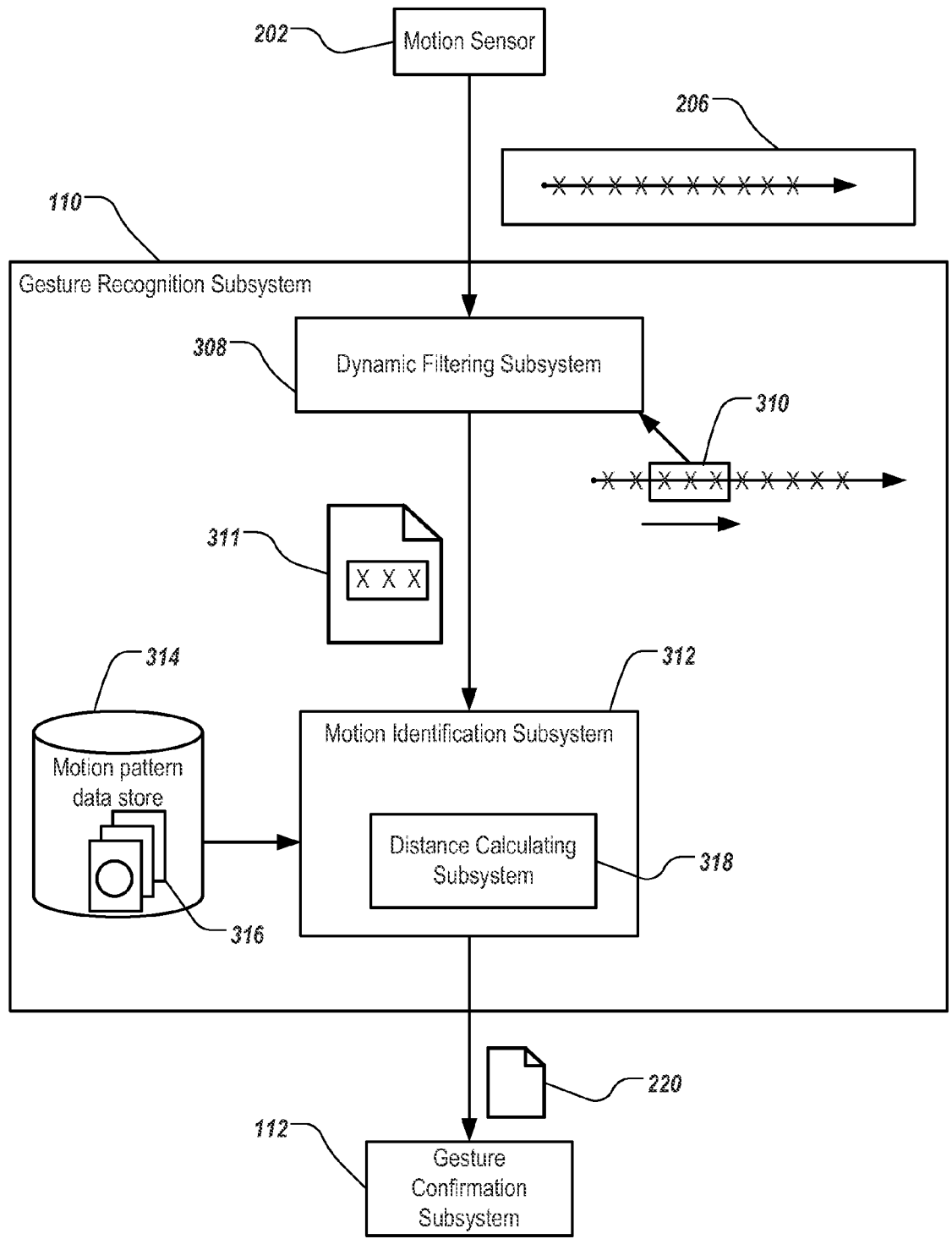
FIG. 3 is a block diagram illustrating an exemplary system of gesture recognition.

FIG. 3 is a block diagram illustrating an exemplary system of gesture recognition. The system of gesture recognition can include motion sensor 202 and gesture recognition subsystem 110. Gesture recognition subsystem 110 can be configured to receive and process motion sensor readings 206. Gesture recognition subsystem 110 can include dynamic filtering subsystem 308. Dynamic filtering subsystem 308 is a component of the gesture recognition subsystem 110 that is configured to perform dynamic filtering on motion sensor readings 206. Dynamic filtering subsystem 308 can high-pass filter each of the motion sensor readings 206. Dynamic filtering subsystem 308 can reduce a time dimension of the time series of motion vectors in the motion sensor readings 206.

In some implementations, dynamic filtering subsystem 308 can apply a filtering threshold, which can be at least one of an acceleration value or an angular rate value. If a motion vector V exceeds the filtering threshold on at least one axis (e.g., axis X), dynamic filtering subsystem 308 can process a series of one or more motion vectors V1 ... Vi that precede the motion vector V in time to generate a new motion vector V' for replacing motion vectors V1 ... Vi. Dynamic filtering subsystem 308 can generate motion vector V' by calculating an average of vectors V1 ... Vi. Thus, dynamic filtering subsystem 308 can create normalized motion sensor readings that has fewer items in the time series.

In addition, dynamic filtering subsystem 308 can be configured to select a portion of motion sensor readings 206 for further processing. The selection can be based on sliding time window 310. Motion sensor 202 can generate motion sensor readings 206 continuously. Dynamic filtering subsystem 308 can use the sliding window 310 to select segments of the continuous data, and generate normalized motion sensor readings 311 based on the selected segments.

Gesture recognition subsystem 110 can include motion identification subsystem 312. Motion identification subsystem 312 is a component of gesture recognition subsystem 110 that is configured to determine whether normalized motion sensor readings 311 matches a known motion pattern. Motion identification subsystem 312 can receive normalized motion sensor readings 311, and access motion pattern data store 314. Motion pattern data store 314 can include a storage device that stores one or more motion patterns 316. Each of motion patterns 316 can include a series of motion vectors and be associated with a sphere of influence (SOI) that defines an error margin. Motion identification subsystem 312 can compare the received normalized motion sensor readings 311 with each of the stored motion patterns 316, and recognize a gesture based on the comparison.

Comparing the received normalized motion sensor readings 311 with each of the stored motion patterns 316 can include a distance calculation. Motion identification subsystem 312 can include distance-calculating subsystem 318. Distance calculating subsystem 318 is a component of motion identification subsystem 312 that is configured to calculate a distance between normalized motion sensor readings 311 and each of the motion patterns 316. If the distance between normalized motion sensor readings 311 and a motion pattern P is within the radius of an SOI of the motion pattern P, motion identification subsystem 312 can identify a match and recognize gesture 220. Motion identification subsystem 312 can send the recognized gesture 220 to proximity detection subsystem 112. Further details of the operations of distance calculating subsystem 318 will be described below in reference to FIGS. 4A-4B.

Figure 4A:
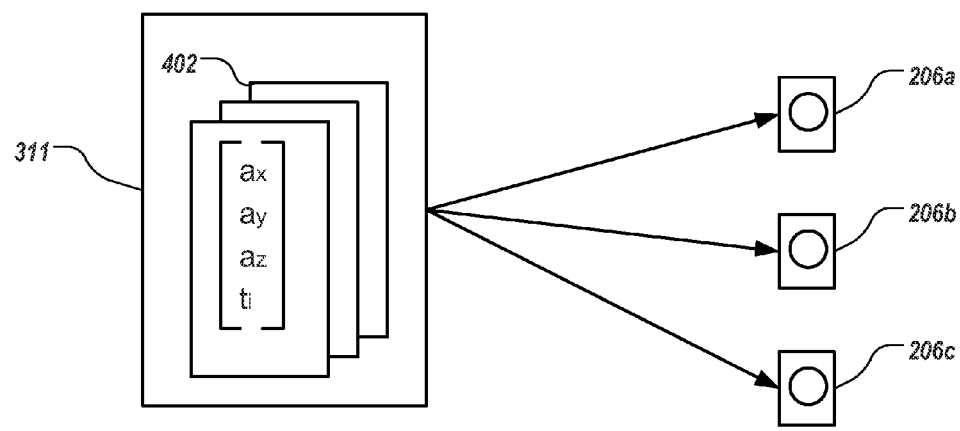
FIGS. 4A-4B are diagrams illustrating exemplary techniques of matching motion sensor readings to a motion pattern.
Figure 4B:
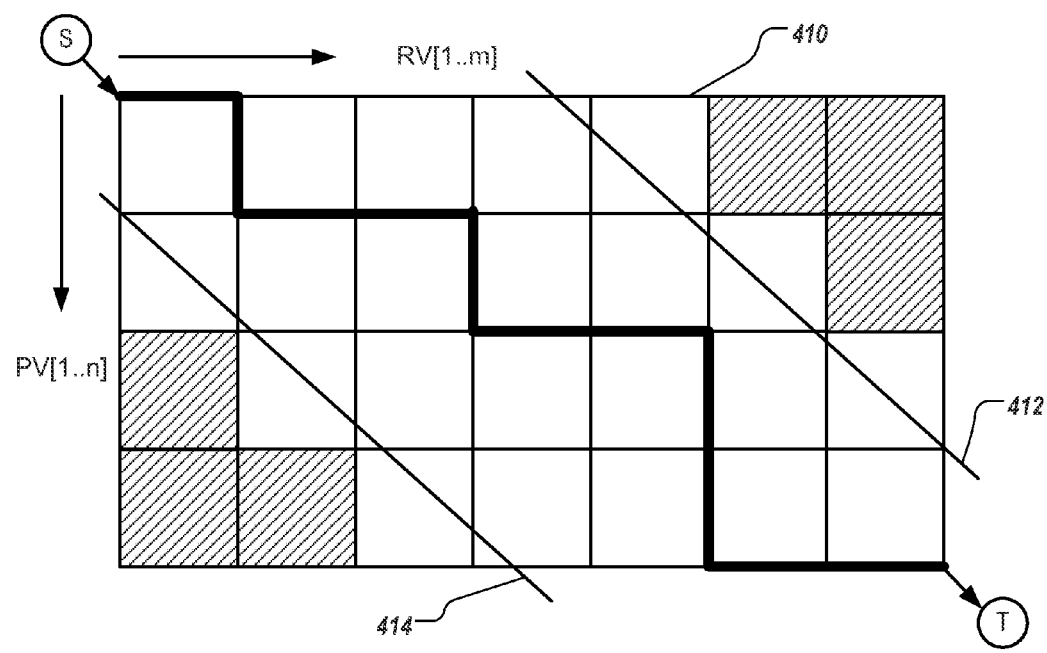

FIGS. 4A-4B are diagrams illustrating exemplary techniques of matching motion sensor readings to a motion pattern. FIG. 4A illustrates an example data structure of normalized motion sensor readings 311 as described in reference to FIG. 3 above. Normalized motion sensor readings 311 can include a series of motion vectors 402. Each motion vector 402 can include acceleration readings or angular rates $a_x$, $a_y$, and $a_z$, for axes X, Y, and Z, respectively. In some implementations, each motion vector 402 can be associated with a time $t_i$, the time defining the time series. In some implementations, the normalized motion sensor readings 311 can implicitly designate the time dimension of the time series using an order of the motion vectors 402. In these implementations, the time can be omitted.

Distance calculating subsystem 318 (as described above in reference to FIG. 3) can compare normalized motion sensor readings 311 to each of motion patterns 206a, 206b, and 206c. The comparison can produce a match. If normalized motion sensor readings 311 matches at least one of motion patterns 206a, 206b, and 206c, a gesture is tentatively recognized. The operations of comparison are described in further detail below in reference to FIG. 4B.

FIG. 4B is a diagram illustrating distance calculating operations of distance calculating subsystem 318. To perform the comparison, distance-calculating subsystem 318 can calculate a distance between the normalized motion sensor readings 311 and a motion pattern (e.g., motion pattern 206a, 206b, or 206c). Distance calculating subsystem 318 can calculate the distance using directed graph 410 using dynamic time warp techniques between normalized motion sensor readings 311 and a motion pattern. For convenience, the normalized motion sensor readings 311 will be designated as R and the motion pattern will be designated as P. The distance between R and P will be designated as D(R, P).

In the example shown, normalized motion sensor readings 311 can include a time series of m normalized motion sensor readings RV(1) through RV(m). The motion pattern can include a time series of n motion vectors PV(1) through PV(n). In some implementations, the distance calculating subsystem 318 calculates the distance D(R, P) by employing directed graph 410. Directed graph 410 can include m×n nodes. Each node can be associated with a cost. The cost of a node (i, j) can be determined based on a distance between motion vectors RV(i) and PV(j). The distance can be a Euclidean distance, a Manhattan distance, or any other distance between two vectors in a multi-dimensional space.

Distance calculating subsystem 318 can add a directed edge from a node (i, j) to a node (i, j+1) and from the node (i, j) to a node (i+1, j). The directed edges between all nodes thus can form a grid, in which, in this example, multiple paths leads from the node (1, 1) to the node (m, n).

Distance calculating subsystem 318 can add, to directed graph 410, a source node S and a directed edge from S to node (1, 1), and target node T and a directed edge from node (m, n) to T. Distance calculating subsystem 318 can determine a shortest path between S and T, and designate the cost of the shortest path as the distance D(R, P) between R and P.

In some implementations, distance-calculating subsystem 318 can perform optimization on the comparing. Distance calculating subsystem 318 can perform the optimization by applying comparison thresholds 412 and 414. Comparison thresholds 412 and 414 can define a series of vector pairs between which distance-calculating subsystem 318 performs a distance calculation. By applying comparison thresholds 412 and 414, distance-calculating subsystem 318 can exclude those calculations that are unlikely to lead to a match. For example, a distance calculation between the first motion vector RV(1) in the normalized motion sensor readings 311 and a last motion vector PV(n) of a motion pattern is unlikely to lead to a match, and therefore can be omitted from the calculations.

Distance calculating subsystem 318 can compare the distance D(R, P) with a SOI associated with motion pattern P. If the distance is within the SOI, distance-calculating subsystem 318 can identify a match. A gesture can be tentatively recognized.

Figure 5:
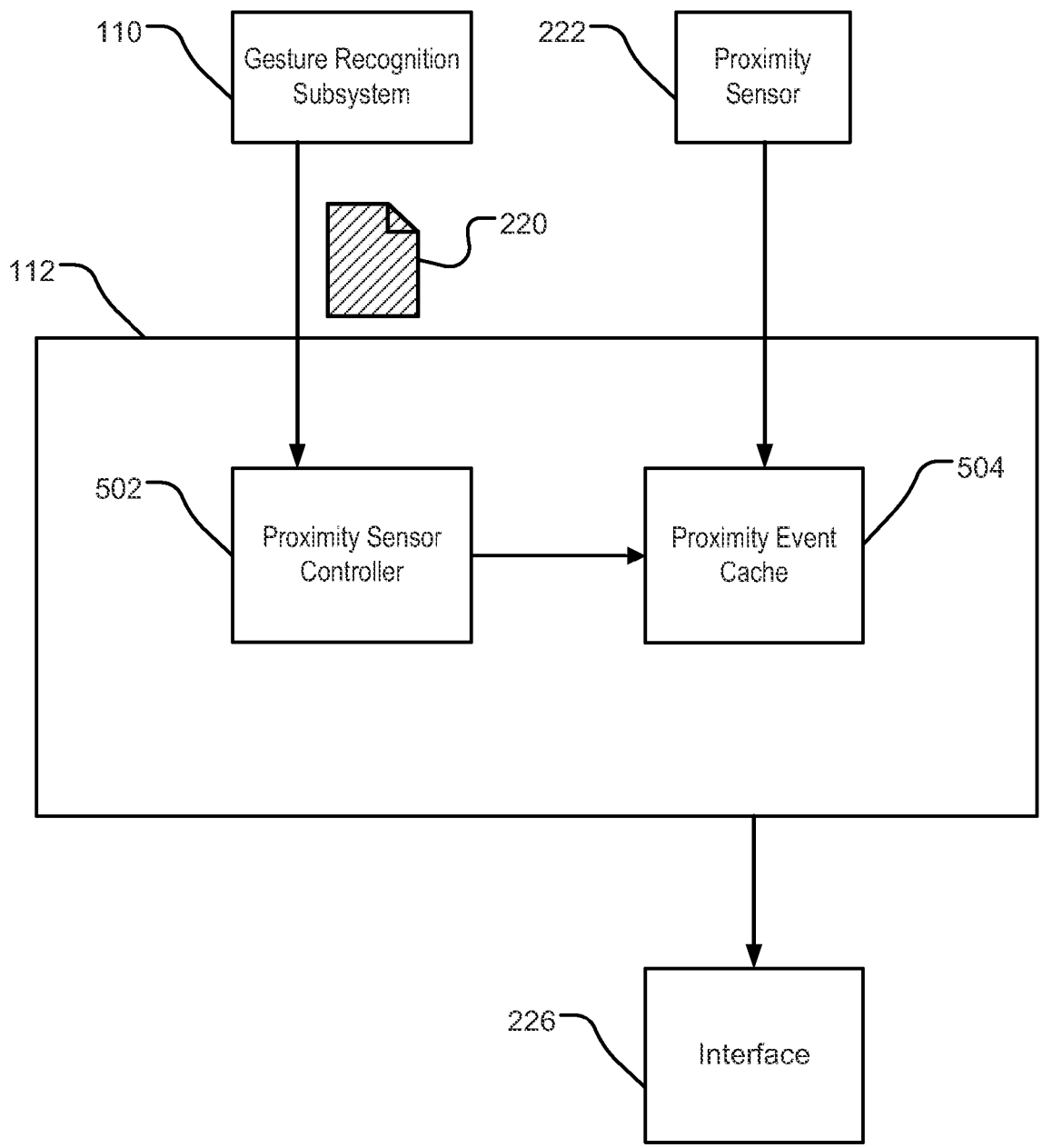
FIG. 5 is a block diagram illustrating an exemplary gesture confirmation subsystem of a mobile device.

FIG. 5 is a block diagram illustrating exemplary proximity detection subsystem 112 of mobile device 100. Proximity detection subsystem 112 can be configured to confirm the tentatively recognized gesture. Proximity detection subsystem 112 can include a proximity sensor controller 502. Proximity sensor controller 502 is a component of proximity detection subsystem 112 that can set proximity sensor 222 to various operating modes based on recognized gesture 220 as received from gesture recognition subsystem 110.

To detect that mobile device 100 is in proximity to an object, proximity sensor 222 can emit an electromagnetic or electrostatic field and detect a change in the field. To detect the change, proximity sensor 222 can compare a reading of the field to a baseline. The baseline can be a reading of the electromagnetic or electrostatic field when no object is in detectable proximity of the proximity sensor. If an offset between the reading and the baseline satisfies a threshold, a proximity event can be detected.

Proximity sensor controller 502 can configure proximity sensor 222 to operate in a passive mode or an active mode. When proximity sensor 222 operates in a passive mode, proximity detection subsystem 112 can store a representation of the proximity event and (e.g., a timestamp of the occurrence of the proximity event) in proximity event cache 504. Proximity detection subsystem 112 can send a signal to interface 226 when a time difference between a timestamp of recognized gesture 220 and the timestamp of the occurrence of the proximity event is smaller than a threshold. When proximity sensor 222 operates in an active mode, proximity detection subsystem 112 can send a signal to interface 226 when proximity sensor 222 detects a proximity event.

Proximity sensor controller 502 can set proximity sensor 222 to passive mode by default. Proximity sensor controller 502 can set proximity sensor 222 to active mode when proximity sensor controller 502 receives recognized gesture 220 from gesture recognition subsystem 110. Proximity sensor controller 502 can set proximity sensor 222 back to passive mode when proximity detection subsystem 112 sends the signal to interface 226. Additionally, proximity sensor controller 502 can set proximity sensor 222 back to passive mode when, after a threshold time has passed since proximity sensor 222 is set to an active mode, proximity sensor 222 does not detect a proximity event.

Figure 6A:
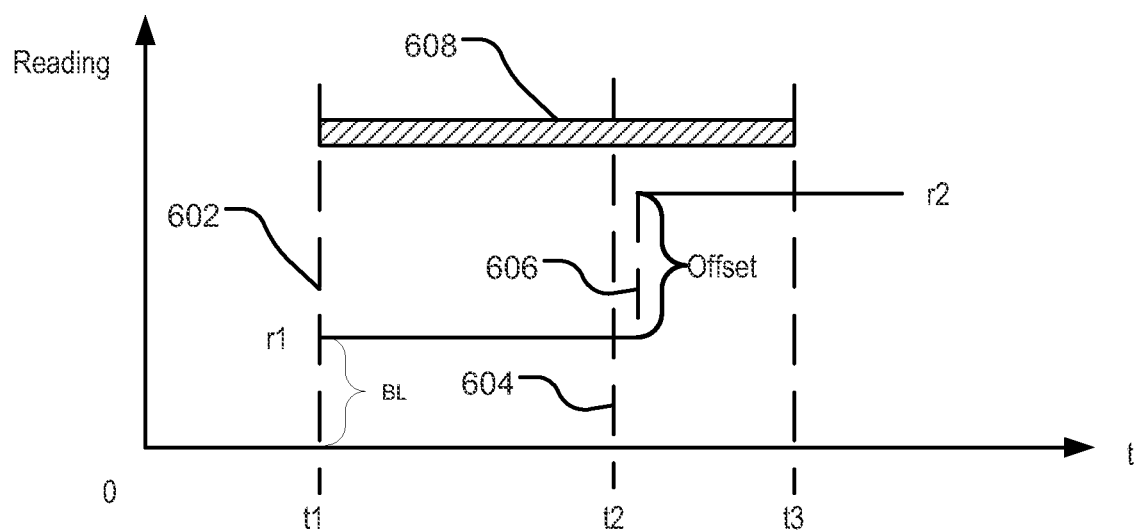
FIGS. 6A-6B are diagrams illustrating timelines of configuring a proximity sensor.
Figure 6B:
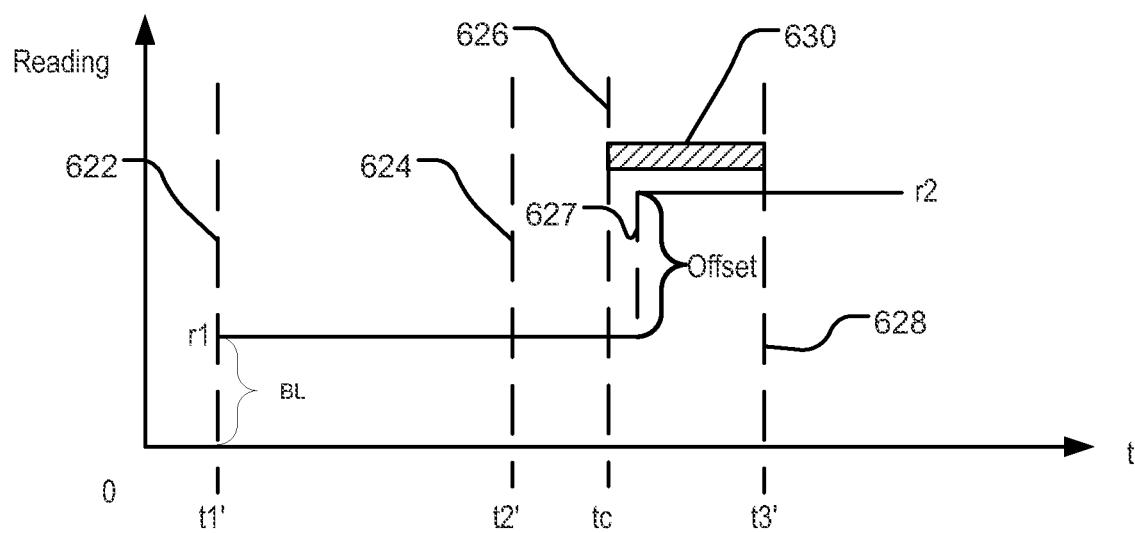

FIGS. 6A-6B are diagrams illustrating timelines of configuring a proximity sensor. FIG. 6A illustrates conventional operations of a proximity sensor of a mobile device. At time a (602), the mobile device can activate a proximity sensor for a task that requests proximity sensor input. The proximity sensor can emit an electromagnetic or electrostatic field. At time t2 (604), the proximity sensor can acquire sufficient readings to establish a baseline r1 against which a change can be measured. The time taken to acquire the baseline is (t2-t1). At time 606, the mobile device moves close to an object. The electromagnetic or electrostatic field changes to r2. At time t3, the proximity sensor can detect the change. The proximity sensor can determine that the offset between r2 and r1 satisfies a proximity threshold, and can determine that the mobile device has moved to a proximity of an object. Perceived response time 608 is thus the time of establishing the baseline (t2-t1) plus the time for proximity detection (t3-t2).

Figure 7A:
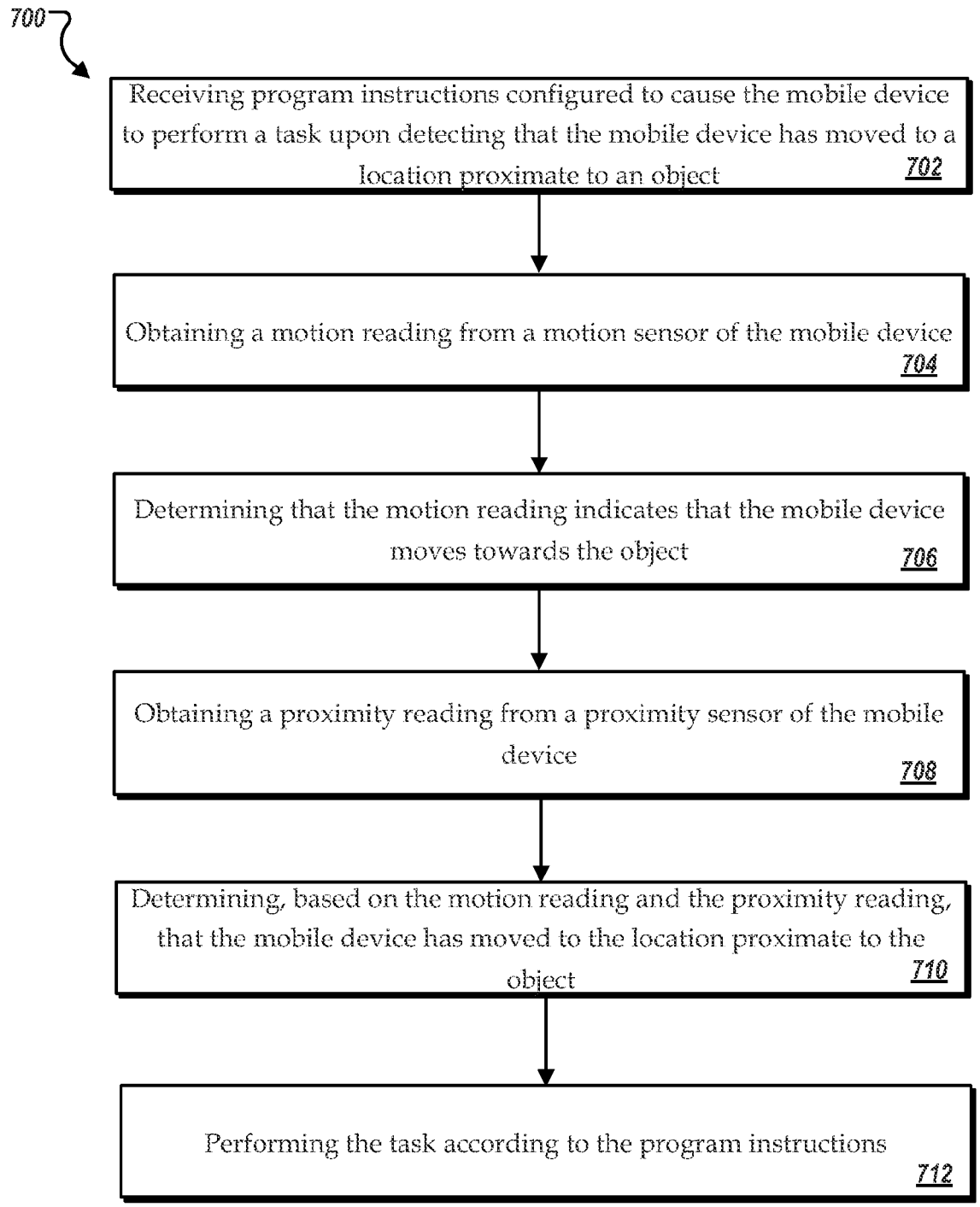
FIG. 7A-7C are flowcharts illustrating exemplary motion-based operations of a mobile device.

FIG. 6B illustrates motion-based operations of a proximity sensor of a mobile device. At time t1' (622), the mobile device can enter a motion detection mode. A proximity sensor can be turned on and set to operate in a passive mode. In the passive mode, the proximity sensor can establish a baseline. At time t2' (624), the proximity sensor establishes the baseline r1. The time taken to acquire the baseline is (t2't1'). At time tc (626), a gesture recognition subsystem detects a gesture and upon such detection, a gesture configuration system sets the proximity sensor to an active mode. Subsequently, at time 627, the electromagnetic or electrostatic field changes to r2. At time t3' (628), the motion sensor can determine that the offset between r2 and r1 satisfies a proximity threshold, and determines that the mobile device has moved to a location that is proximate to an object. The time for establishing the baseline (t2'-t1') can be masked by time taken by the motion of the mobile device (e.g., the time it takes to pick up the mobile device and put the mobile device near an ear). Accordingly, perceived response time 630 can be proximity detection time (t3'-tc), which can be hundreds of milliseconds shorter than perceived response time 608 (of FIG. 6A) of a conventional mobile device Exemplary Motion-Based Operations of a Mobile Device FIG. 7A is a flowchart illustrating exemplary motion-based operations 700 of a mobile device. The mobile device can be mobile device 100 as described above. The mobile device can receive (702) program instructions configured to cause the mobile device to perform a task upon detecting that the mobile device has moved to a location proximate to an object. The object can include at least a portion of a human face. The program instructions can include operation system instructions, application program instructions, or both. The program instructions can be configured to cause the mobile device to operate in a touch input mode for receiving a touch input, or a speech input mode for receiving a speech input.

The mobile device can obtain (704) a motion reading from a motion sensor of the mobile device. While obtaining the motion reading from the motion sensor of the mobile device, the mobile device can determine a proximity baseline for the proximity sensor. Determining the proximity baseline for the proximity sensor of the mobile device can include setting the proximity sensor to a passive mode in which the proximity sensor generates one or more baseline readings, and determining the proximity baseline based on the baseline readings generated by the proximity sensor in the passive mode.

The mobile device can determine (706) that the motion reading indicates that the mobile device moves towards the object. Determining that the motion reading indicates that the mobile device moves towards the object can include comparing the motion reading to one or more pre-stored motion patterns, and determining that the mobile device is moving in a gesture towards the object based on a result of the comparing. The one or more pre-stored motion patterns can be associated with a gesture of moving the mobile device toward the object. Each pre-stored motion pattern can correspond to a manner of movement of the gesture.

In response to determining the motion reading indicates that the mobile device moves towards the object, the mobile device can obtain (708) a proximity reading from a proximity sensor of the mobile device. Obtaining the proximity reading can include setting the proximity sensor from the passive mode to an active mode in which the proximity sensor generates one or more readings for comparing with the proximity baseline. Determining that the motion reading indicates that the mobile device moves towards the object includes determining a motion beginning time. Setting the proximity sensor from the passive mode to the active mode occurs after a specified delay from the motion beginning time.

Based on the motion reading and the proximity reading, the mobile device can determine (710) that the mobile device has moved to the location proximate to the object. Determining that the mobile device has moved to the location proximate to the object can include determining that the proximity reading satisfies a specified proximity offset from the proximity baseline.

The mobile device can perform (712) the task according to the program instructions. Performing the task can include changing an input mode of the mobile device from the touch input mode to the speech input mode. Changing the input mode to the speech input mode includes configuring the mobile device to accept at least one of a speech command or a dictation.

Figure 7B:
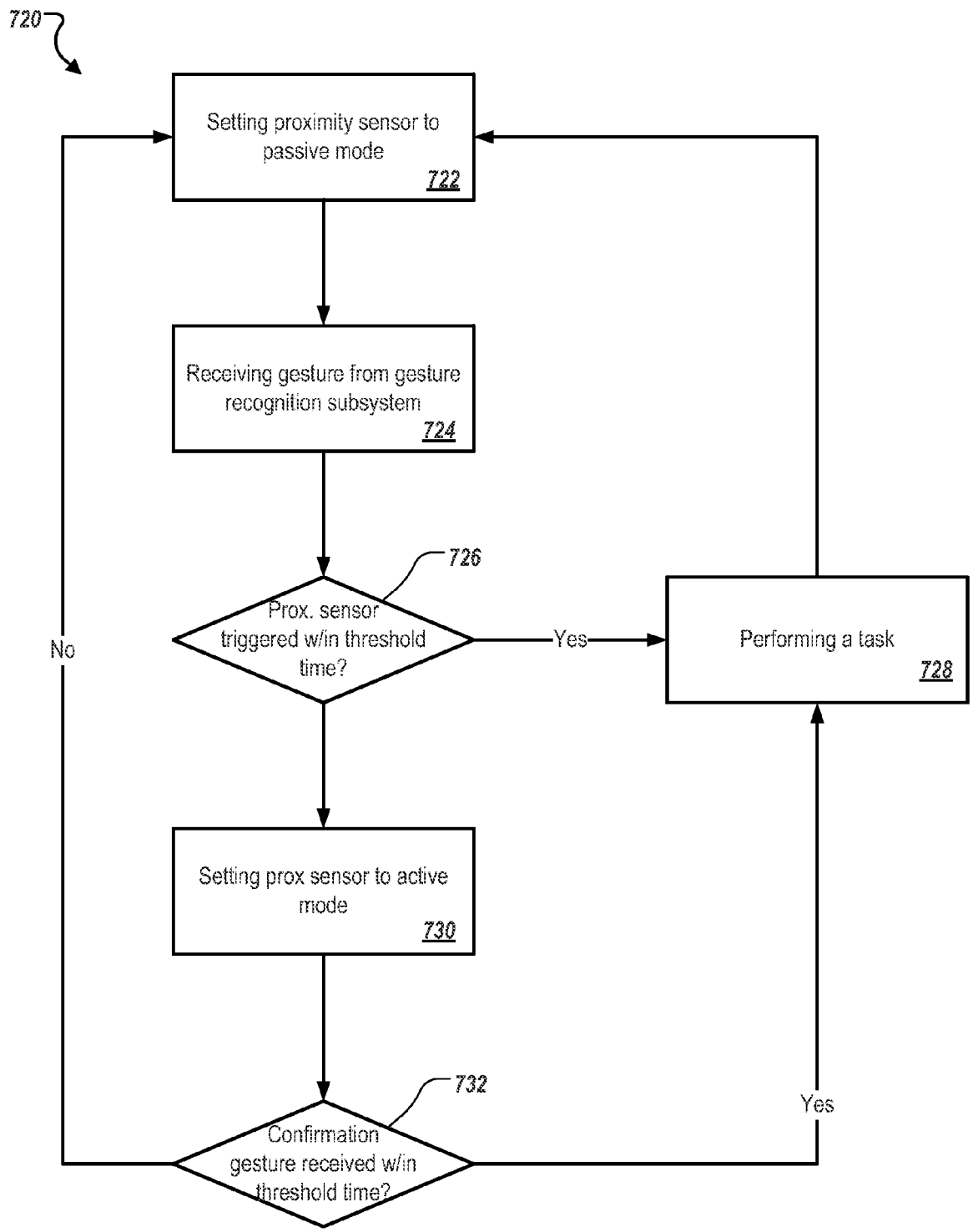

FIG. 7B is a flowchart illustrating exemplary motion-based operations 720 of a mobile device. The mobile device can be mobile device 100 as described above. The mobile device can set (722) a proximity sensor to operate in a passive mode.

The mobile device can receive (724) a recognized gesture from a gesture recognition subsystem of the mobile device. The mobile device can determine (726) whether the proximity sensor detected a proximity event within a threshold time period (e.g., 100 milliseconds) before receiving the recognized gesture.

If the mobile device determines that the proximity sensor detected a proximity event within a threshold time period before receiving the recognized gesture, the mobile device can confirm the proximity event. Upon confirmation, mobile device can perform (728) a task (e.g., changing an input mode to voice input mode). In addition to performing the task, the mobile device can set (722) the proximity sensor back to passive mode.

If the mobile device determines that the proximity sensor did not detect a proximity event within a threshold time period before receiving the recognized gesture, the mobile device can set (730) the proximity sensor to operate in an active mode. The mobile device can determine (732) whether the proximity sensor has detected a proximity event within a threshold time period (e.g., 100 milliseconds) after receiving the recognized gesture. If the proximity sensor has detected a proximity event within a threshold time period after receiving the recognized gesture, the mobile device can perform (728)

the task. Otherwise, the mobile device can set (722) the proximity sensor to operate in passive mode.

Figure 7C:
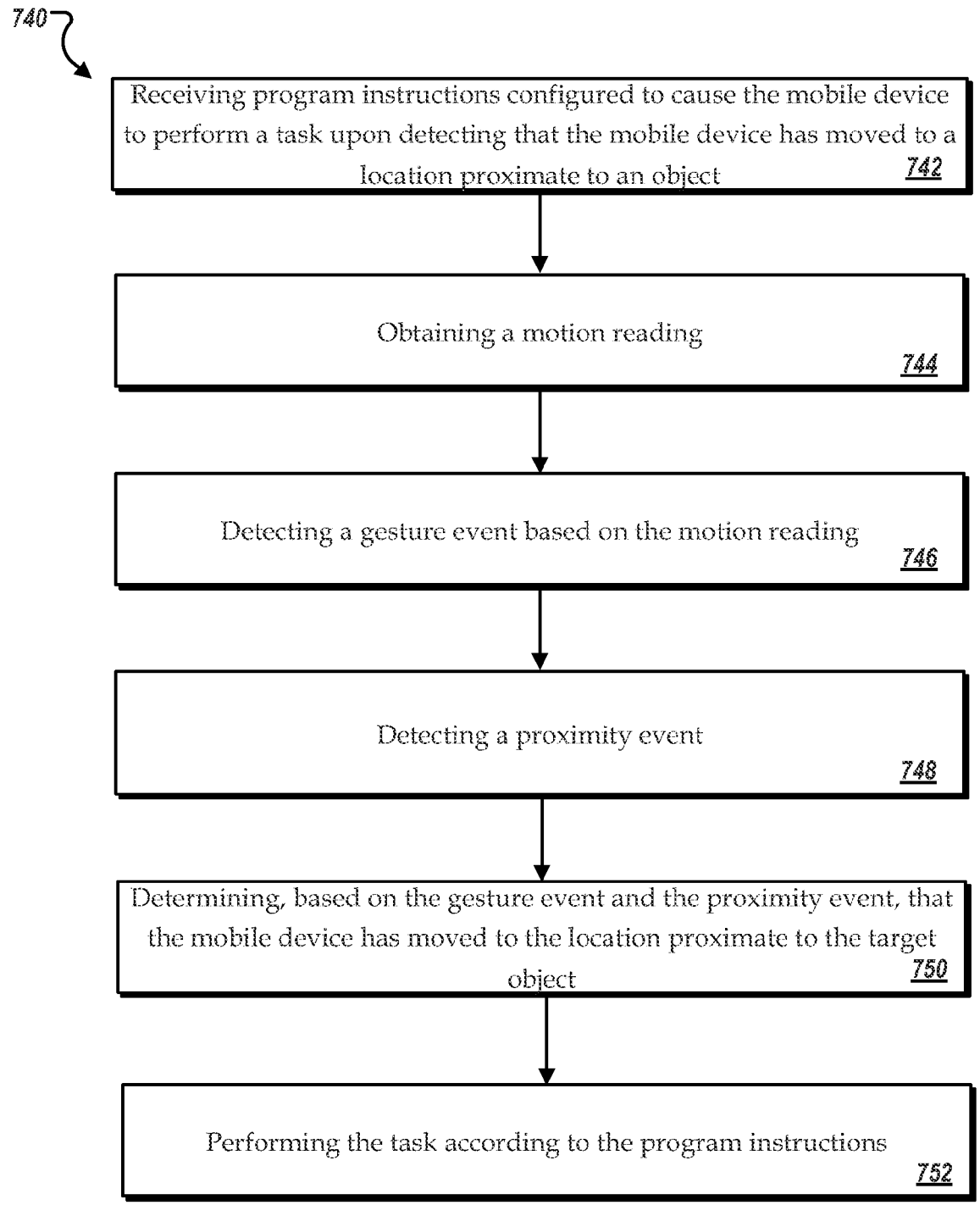

FIG. 7C is a flowchart illustrating exemplary motion-based operations 740 of a mobile device. The mobile device can be mobile device 100 as described above. The mobile device can receive (742) program instructions configured to cause the mobile device to perform a task upon detecting that the mobile device has moved to a location proximate to an object.

The mobile device can obtain (744) a motion reading from one or more motion sensing devices of the mobile device. The motion sensing devices can include at least one of an accelerometer, a gyroscope, a magnetometer, a light sensor, or a gravimeter.

The mobile device can detect (746) a gesture event based on the motion reading. Detecting the gesture event can include determining that the motion reading indicates that the mobile device moves towards a target object in one or more specified fashions.

The mobile device can detect (748) a proximity event. Detecting the proximity event can include obtaining a proximity reading from a proximity sensor of the mobile device. The proximity reading can indicate that the mobile device is located proximate to an object. Detecting the proximity event can include setting the proximity sensor to operate in a passive mode in which a trigger of the proximity sensor causes an event notification of a proximity event. Detecting the proximity event can include detecting the proximity event when the proximity sensor operates in the passive mode.

The mobile device can determine (750), based on the gesture event and the proximity event, that the mobile device has moved to the location proximate to the target object. Determining that the mobile device has moved to the location proximate to the target object can include determining that the mobile device has moved to the location proximate to the target object when the proximity event is detected within a threshold time period before detecting the gesture event, or when the proximity event is detected within a threshold time period after detecting the gesture event. Determining that the mobile device has moved to the location proximate to the target object can include setting the proximity sensor to switch from a passive mode to an active mode upon detection of the gesture event. When operating in the active mode, a trigger of the proximity sensor can cause an event notification of a proximity event, a turning off of a backlight of a display, or a turning off of a touch input of a touch-sensitive input device.

The mobile device can perform (752) the task according to the program instructions. The task can include turning off a touch-sensitive display screen and switching an input mode of the mobile device between touch input mode and voice input mode.

Exemplary Mobile Device Architecture

Figure 8:
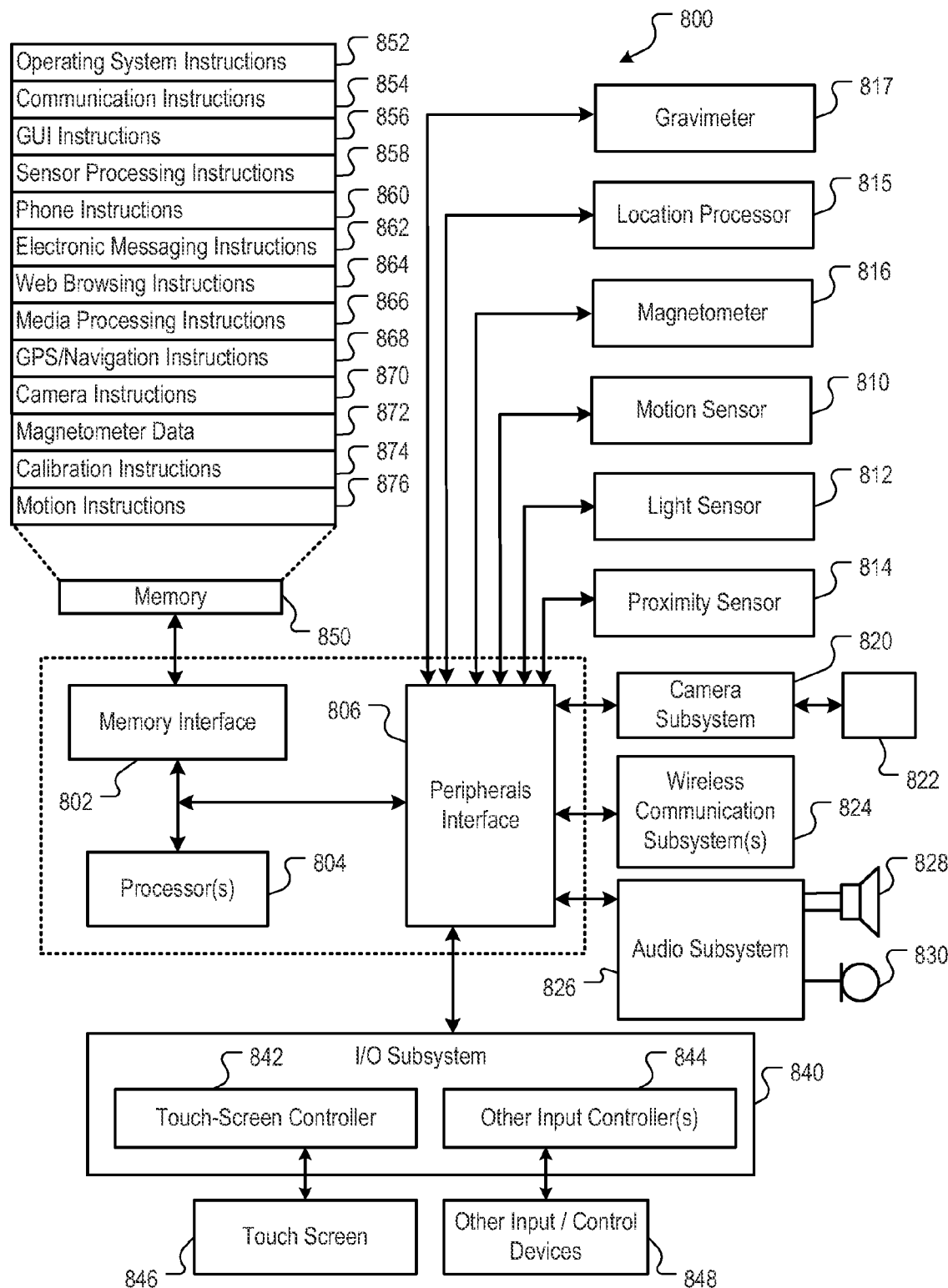
FIG. 8 is a block diagram of exemplary architecture of a mobile device configured to perform motion-based operations.

FIG. 8 is a block diagram of exemplary architecture 800 of a mobile device configured to perform motion-based operations. A mobile device can include memory interface 802, one or more data processors, image processors and/or processors 804, and peripherals interface 806. Memory interface 802, one or more processors 804 and/or peripherals interface 806 can be separate components or can be integrated in one or more integrated circuits. Processors 804 can include one or more application processors (APs) and one or more baseband processors (BPs). The application processors and baseband processors can be integrated in one single process chip. The various components in mobile device 100, for example, can be coupled by one or more communication buses or signal lines.

Sensors, devices, and subsystems can be coupled to peripherals interface 806 to facilitate multiple functionalities. For example, motion sensor 810, light sensor 812, and proximity sensor 814 can be coupled to peripherals interface 806 to facilitate orientation, lighting, and proximity functions of the mobile device. Motion sensor 810 can include one or more accelerometers configured to determine change of speed and direction of movement of the mobile device. Location processor 815 (e.g., GPS receiver) can be connected to peripherals interface 806 to provide geopositioning. Electronic magnetometer 816 (e.g., an integrated circuit chip) can also be connected to peripherals interface 806 to provide data that can be used to determine the direction of magnetic North. Thus, electronic magnetometer 816 can be used as an electronic compass. Gravimeter 817 can be coupled to peripherals interface 806 to facilitate measurement of a local gravitational field of Earth.

Camera subsystem 820 and an optical sensor 822, e.g., a charged coupled device (CCD) or a complementary metal-oxide semiconductor (CMOS) optical sensor, can be utilized to facilitate camera functions, such as recording photographs and video clips.

Communication functions can be facilitated through one or more wireless communication subsystems 824, which can include radio frequency receivers and transmitters and/or optical (e.g., infrared) receivers and transmitters. The specific design and implementation of the communication subsystem 824 can depend on the communication network(s) over which a mobile device is intended to operate. For example, a mobile device can include communication subsystems 824 designed to operate over a CDMA system, a WiFi™ or WiMax™ network, and a Bluetooth™ network. In particular, the wireless communication subsystems 824 can include hosting protocols such that the mobile device can be configured as a base station for other wireless devices.

Audio subsystem 826 can be coupled to a speaker 828 and a microphone 830 to facilitate voice-enabled functions, such as voice recognition, voice replication, digital recording, and telephony functions.

I/O subsystem 840 can include touch screen controller 842 and/or other input controller(s) 844. Touch-screen controller 842 can be coupled to a touch screen 846 or pad. Touch screen 846 and touch screen controller 842 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with touch screen 846.

Other input controller(s) 844 can be coupled to other input/control devices 848, such as one or more buttons, rocker switches, thumb-wheel, infrared port, USB port, and/or a pointer device such as a stylus. The one or more buttons (not shown) can include an up/down button for volume control of speaker 828 and/or microphone 830.

In one implementation, a pressing of the button for a first duration may disengage a lock of the touch screen 846; and a pressing of the button for a second duration that is longer than the first duration may turn power to mobile device 100 on or off. The user may be able to customize a functionality of one or more of the buttons. The touch screen 846 can, for example, also be used to implement virtual or soft buttons and/or a keyboard.

In some implementations, mobile device 100 can present recorded audio and/or video files, such as MP3, AAC, and MPEG files. In some implementations, mobile device 100 can include the functionality of an MP3 player. Mobile device 100 may, therefore, include a pin connector that is compatible with the iPod. Other input/output and control devices can also be used.

Memory interface 802 can be coupled to memory 850. Memory 850 can include high-speed random access memory and/or non-volatile memory, such as one or more magnetic disk storage devices, one or more optical storage devices, and/or flash memory (e.g., NAND, NOR). Memory 850 can store operating system 852, such as Darwin, RTXC, LINUX, UNIX, OS X, WINDOWS, or an embedded operating system such as VxWorks. Operating system 852 may include instructions for handling basic system services and for performing hardware dependent tasks. In some implementations, operating system 852 can include a kernel (e.g., UNIX kernel).

Memory 850 may also store communication instructions 854 to facilitate communicating with one or more additional devices, one or more computers and/or one or more servers. Memory 850 may include graphical user interface instructions 856 to facilitate graphic user interface processing; sensor processing instructions 858 to facilitate sensor-related processing and functions; phone instructions 860 to facilitate phone-related processes and functions; electronic messaging instructions 862 to facilitate electronic-messaging related processes and functions; web browsing instructions 864 to facilitate web browsing-related processes and functions; media processing instructions 866 to facilitate media processing-related processes and functions; GPS/Navigation instructions 868 to facilitate GPS and navigation-related processes and instructions; camera instructions 870 to facilitate camera-related processes and functions; magnetometer data 872 and calibration instructions 874 to facilitate magnetometer calibration. The memory 850 may also store other software instructions (not shown), such as security instructions, web video instructions to facilitate web video-related processes and functions, and/or web shopping instructions to facilitate web shopping-related processes and functions. In some implementations, the media processing instructions 866 are divided into audio processing instructions and video processing instructions to facilitate audio processing-related processes and functions and video processing-related processes and functions, respectively. An activation record and International Mobile Equipment Identity (IMEI) or similar hardware identifier can also be stored in memory 850. Memory 850 can include location instructions 876. Motion instructions 876 can be a computer program product that is configured to cause the mobile device to perform motion-based operations, including gesture recognition operations and gesture confirmation operations, as described in reference to FIGS. 1-7.

Each of the above identified instructions and applications can correspond to a set of instructions for performing one or more functions described above. These instructions need not be implemented as separate software programs, procedures, or modules. Memory 850 can include additional instructions or fewer instructions. Furthermore, various functions of the mobile device may be implemented in hardware and/or in software, including in one or more signal processing and/or application specific integrated circuits.

Exemplary Operating Environment

FIG. 9 is a block diagram of exemplary network operating environment 900 for the mobile devices configured to perform motion-based operations. Mobile devices 902a and 902b can, for example, communicate over one or more wired and/or wireless networks 910 in data communication. For example, a wireless network 912, e.g., a cellular network, can communicate with a wide area network (WAN) 914, such as the Internet, by use of a gateway 916. Likewise, an access device 918, such as an 802.11g wireless access device, can provide communication access to the wide area network 914.

In some implementations, both voice and data communications can be established over wireless network 912 and the access device 918. For example, mobile device 902a can place and receive phone calls (e.g., using voice over Internet Protocol (VoIP) protocols), send and receive e-mail messages (e.g., using Post Office Protocol 3 (POP3)), and retrieve electronic documents and/or streams, such as web pages, photographs, and videos, over wireless network 912, gateway 916, and wide area network 914 (e.g., using Transmission Control Protocol/Internet Protocol (TCP/IP) or User Datagram Protocol (UDP)). Likewise, in some implementations, the mobile device 902b can place and receive phone calls, send and receive e-mail messages, and retrieve electronic documents over the access device 918 and the wide area network 914. In some implementations, mobile device 902a or 902b can be physically connected to the access device 918 using one or more cables and the access device 918 can be a personal computer. In this configuration, mobile device 902a or 902b can be referred to as a "tethered" device.

Mobile devices 902a and 902b can also establish communications by other means. For example, wireless mobile device 902a can communicate with other wireless devices, e.g., other mobile devices 902a or 902b, cell phones, etc., over the wireless network 912. Likewise, mobile devices 902a and 902b can establish peer-to-peer communications 920, e.g., a personal area network, by use of one or more communication subsystems, such as the Bluetooth™ communication devices. Other communication protocols and topologies can also be implemented.

The mobile device 902a or 902b can, for example, communicate with one or more services 930 and 940 over the one or more wired and/or wireless networks. For example, one or more motion training services 930 can be used to determine one or more motion patterns. Motion pattern service 940 can provide the one or more one or more motion patterns to mobile devices 902a and 902b for recognizing gestures.

Mobile device 902a or 902b can also access other data and content over the one or more wired and/or wireless networks. For example, content publishers, such as news sites, Rally Simple Syndication (RSS) feeds, web sites, blogs, social networking sites, developer networks, etc., can be accessed by mobile device 902a or 902b. Such access can be provided by invocation of a web browsing function or application (e.g., a browser) in response to a user touching, for example, a Web object.

A number of implementations of the invention have been described. Nevertheless, it will be understood that various modifications can be made without departing from the spirit and scope of the invention. For example, each subsystem, component, or unit described above can include a hardware device, software instructions, or both.

What is claimed is:

1. A method, comprising:
   at a time a mobile device enters a motion detection mode, turning on a proximity sensor of the mobile device and setting the proximity sensor to operate in a passive mode, wherein in the passive mode, the mobile device establishes a baseline of the proximity sensor, the baseline comprising a proximity reading indicating that the proximity sensor does not detect an object, the baseline usable by the mobile device to determine proximity with an object upon determining that proximity readings of the proximity sensor satisfy a specified offset from the baseline;

obtaining a motion reading from one or more motion sensing devices of the mobile device during a time that the mobile device operates in the motion detection mode;

while obtaining the motion reading, and prior to a gesture is recognized from the motion reading, acquiring a plurality of readings of the proximity sensor for establishing the baseline and establishing the baseline from the plurality of readings;

after setting the proximity sensor to the passive operating mode, recognizing the gesture, including determining that the motion reading indicates that the mobile device moves towards a target object in one or more specified fashions;

after recognizing the gesture, performing actions comprising:
  setting the proximity sensor to operate to an active operating mode;
  determining that a difference between a reading of the proximity sensor obtained in the active operating mode and the baseline determined by the proximity sensor before the gesture was recognized satisfies a threshold value; and
  in response, confirming that the gesture is not a false positive; and then performing a task in response to the confirmed gesture, wherein time taken to establish the baseline is masked by time during which the mobile device is in motion.

2. The method of claim 1, wherein:
performing the task includes changing an input mode of the mobile device from a touch input mode to a speech input mode.

3. The method of claim 2, wherein changing the input mode to the speech input mode includes configuring the mobile device to accept at least one of a speech command or a dictation.

4. The method of claim 1, wherein recognizing the gesture comprises:
  comparing the motion reading to one or more pre-stored motion patterns, the one or more pre-stored motion patterns being associated with a gesture of moving the mobile device toward the target object, each pre-stored motion pattern corresponding to a manner of movement of the gesture; and
  recognizing the gesture based on results of the comparing.

5. The method of claim 1, wherein, when operating in the active operating mode, a trigger of the proximity sensor causes an event notification of a proximity event, a turning off of a backlight of a display, and a turning off of a touch input of a touch-sensitive input device.

6. The method of claim 5, wherein confirming that the gesture is not a false positive comprises determining that the reading of the proximity sensor obtained in the active operating mode is obtained within a threshold time period after recognizing the gesture.

7. The method of claim 1, wherein the target object includes at least a portion of a human face.

8. The method of claim 1, wherein the one or more motion sensing devices include at least one of an accelerometer, a gyroscope, a magnetometer, a light sensor, or a gravimeter.

9. A non-transitory storage device storing a computer product configured to cause one or more mobile devices to perform operations comprising:
  at a time a mobile device enters a motion detection mode, turning on a proximity sensor of the mobile device and setting the proximity sensor to operate in a passive mode, wherein in the passive mode, the mobile device establishes a baseline of the proximity sensor, the baseline comprising a proximity reading indicating that the proximity sensor does not detect an object, the baseline usable by the mobile device to determine proximity with an object upon determining that proximity readings of the proximity sensor satisfy a specified offset from the baseline;
  obtaining a motion reading from one or more motion sensing devices of the mobile device during a time that the mobile device operates in the motion detection mode;
  while obtaining the motion reading, and prior to a gesture is recognized from the motion reading, acquiring a plurality of readings of the proximity sensor for establishing the baseline and establishing the baseline from the plurality of readings;
  after setting the proximity sensor to the passive operating mode, recognizing the gesture, including determining that the motion reading indicates that the mobile device moves towards a target object in one or more specified fashions;
  after recognizing the gesture, performing actions comprising:
    setting the proximity sensor to operate to an active operating mode;
    determining that a difference between a reading of the proximity sensor obtained in the active operating mode and the baseline determined by the proximity sensor before the gesture was recognized satisfies a threshold value; and
    in response, confirming that the gesture is not a false positive; and then
  performing a task in response to the confirmed gesture, wherein time taken to establish the baseline is masked by time during which the mobile device is in motion.

10. The non-transitory storage device of claim 9, wherein:
performing the task includes changing an input mode of the mobile device from a touch input mode to a speech input mode.

11. The non-transitory storage device of claim 10, wherein changing the input mode to the speech input mode includes configuring the mobile device to accept at least one of a speech command or a dictation.

12. The non-transitory storage device of claim 9, wherein recognizing the gesture comprises:
  comparing the motion reading to one or more pre-stored motion patterns, the one or more pre-stored motion patterns being associated with a gesture of moving the mobile device toward the target object, each pre-stored motion pattern corresponding to a manner of movement of the gesture; and
  recognizing the gesture based on results of the comparing.

13. The non-transitory storage device of claim 9, wherein, when operating in the active operating mode, a trigger of the proximity sensor causes an event notification of a proximity event, a turning off of a backlight of a display, and a turning off of a touch input of a touch-sensitive input device.

14. The non-transitory storage device of claim 13, wherein confirming that the gesture is not a false positive includes determining that the reading the proximity sensor obtained in the active operating mode is obtained within a threshold time period after recognizing the gesture.

15. The non-transitory storage device of claim 9, wherein the target object includes at least a portion of a human face.

16. The non-transitory storage device of claim 9, wherein the one or more motion sensing devices include at least one of an accelerometer, a gyroscope, a magnetometer, a light sensor, or a gravimeter.

17. A system, comprising:
a mobile device configured to perform operations comprising:
at a time the mobile device enters a motion detection mode, turning on a proximity sensor of the mobile device and setting the proximity sensor to operate in a passive mode, wherein in the passive mode, the mobile device establishes a baseline of the proximity sensor, the baseline comprising a proximity reading indicating that the proximity sensor does not detect an object, the baseline usable by the mobile device to determine proximity with an object upon determining that proximity readings of the proximity sensor satisfy a specified offset from the baseline
obtaining a motion reading from one or more motion sensing devices of the mobile device during a time that the mobile device operates in the motion detection mode;
while obtaining the motion reading, and prior to a gesture is recognized from the motion reading, acquiring a plurality of readings of the proximity sensor for establishing the baseline and establishing the baseline from the plurality of readings;
after setting the proximity sensor to the passive operating mode, recognizing a gesture, including determining that the motion reading indicates that the mobile device moves towards a target object in one or more specified fashions;
after recognizing the gesture, performing actions comprising:
setting the proximity sensor to operate to an active operating mode;
determining that a difference between a reading of the proximity sensor obtained in the active operating mode and the baseline determined by the proximity sensor before the gesture was recognized satisfies a threshold value; and
in response, confirming that the gesture is not a false positive; and then
performing a task in response to the confirmed gesture, wherein time taken to establish the baseline is masked by time during which the mobile device is in motion such that user perceived time that elapsed between the mobile device entered the motion detection mode and performing the task excludes the time taken to establish the baseline.

18. The system of claim 17, wherein:
performing the task includes changing an input mode of the mobile device from a touch input mode to a speech input mode.

19. The system of claim 18, wherein changing the input mode to the speech input mode includes configuring the mobile device to accept at least one of a speech command or a dictation.

20. The system of claim 17, wherein recognizing the gesture comprises:
comparing the motion reading to one or more pre-stored motion patterns, the one or more pre-stored motion patterns being associated with a gesture of moving the mobile device toward the target object, each pre-stored motion pattern corresponding to a manner of movement of the gesture; and
recognizing the gesture based on results of the comparing.

21. The system of claim 17, wherein, when operating in the active mode, a trigger of the proximity sensor causes an event notification of a proximity event, a turning off of a backlight of a display, and a turning off of a touch input of a touch-sensitive input device.

22. The system of claim 21, wherein confirming that the gesture is not a false positive includes determining that the reading of the proximity sensor obtained in the active operating mode is obtained within a threshold time period after recognizing the gesture.

23. The system of claim 17, wherein the object includes at least a portion of a human face.

24. The system of claim 17, wherein the one or more motion sensing devices include at least one of an accelerometer, a gyroscope, a magnetometer, a light sensor, or a gravimeter.

* * * * *